(12) United States Patent
Iwase et al.

(10) Patent No.: US 10,789,721 B2
(45) Date of Patent: Sep. 29, 2020

(54) IMAGE PROCESSING APPARATUS, ALIGNMENT METHOD AND STORAGE MEDIUM

(71) Applicant: CANON KABUSHIKI KAISHA, Tokyo (JP)

(72) Inventors: Yoshihiko Iwase, Yokohama (JP); Osamu Sagano, Inagi (JP); Makoto Sato, Tokyo (JP); Hiroki Uchida, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 122 days.

(21) Appl. No.: 16/122,234

(22) Filed: Sep. 5, 2018

(65) Prior Publication Data

US 2019/0073779 A1    Mar. 7, 2019

(30) Foreign Application Priority Data

Sep. 7, 2017    (JP) ................. 2017-172333

(51) Int. Cl.
*G06K 9/00*     (2006.01)
*G06T 7/33*     (2017.01)
*G06T 3/00*     (2006.01)
(Continued)

(52) U.S. Cl.
CPC .............. *G06T 7/337* (2017.01); *A61B 3/102* (2013.01); *G06T 3/0068* (2013.01);
(Continued)

(58) Field of Classification Search
CPC ..... A61B 3/102; A61B 3/0025; A61B 3/1233; A61B 3/10; A61B 3/1225; A61B 3/15; A61B 3/152; A61B 3/0033; A61B 3/12; A61B 5/004; A61B 5/0066; A61B 6/03; A61B 6/032; A61B 6/02; A61B 6/582; A61B 6/587; A61B 8/10; A61B 8/13; A61B 2576/02; A61B 2090/3735; A61B 3090/3762; G06T 7/337; G06T 7/0012; G06T 7/32; G06T 7/30; G06T 7/0014;
(Continued)

(56) References Cited

U.S. PATENT DOCUMENTS 8,938,111 B2 * 1/2015 Kingston ............... A61B 6/032
                                                      128/922
8,958,621 B2 * 2/2015 Lee ........................ A61B 3/102
                                                      382/131
(Continued)

FOREIGN PATENT DOCUMENTS

EP          2693397 A1    2/2014
JP          2010-110392 A1   5/2010
JP          2015-080679 A    4/2015

*Primary Examiner* — Jose L Couso
(74) *Attorney, Agent, or Firm* — Canon U.S.A., Inc. IP Division

(57) ABSTRACT

An image processing apparatus includes first alignment means configured to perform an alignment in a horizontal direction on a plurality of two-dimensional tomographic images based on measurement light controlled to scan an identical position of an eye according to a first method, and second alignment means configured to perform an alignment in a depth direction on the plurality of two-dimensional tomographic images according to a second method that is different from the first method.

20 Claims, 14 Drawing Sheets

(51) Int. Cl.
*G06T 7/00* (2017.01)
*A61B 3/10* (2006.01)

(52) U.S. Cl.
CPC .. *G06T 7/0012* (2013.01); *G06T 2207/10101* (2013.01); *G06T 2207/30041* (2013.01)

(58) Field of Classification Search
CPC ........... G06T 7/97; G06T 7/0016; G06T 7/55; G06T 3/0068; G06T 2207/30041; G06T 2207/10101; G06T 2207/10016; G06T 2207/20216; G06T 2207/10072; G06T 2207/10076; G06T 2207/20221; G06T 2207/20182; G06T 5/50; G06T 5/002; G06T 2211/40; G06T 11/005; G06K 9/0061; G06K 9/00604; G06K 9/6288; G06K 9/6289; G06K 9/6215; G06K 9/00758; G06K 9/00536; G06K 9/32; G06K 2009/00932; G06K 2209/05; G01N 23/046; G01N 2223/419; Y10S 128/922; Y10S 128/923; G01B 9/02082; G01B 9/02083; G01B 9/02091
See application file for complete search history.

(56) References Cited

U.S. PATENT DOCUMENTS

| | | | |
|---|---|---|---|
| 10,478,058 B2 * | 11/2019 | Cheng | G01B 9/02083 |
| 2008/0100612 A1 * | 5/2008 | Dastmalchi | A61B 3/102 345/418 |
| 2011/0205490 A1 | 8/2011 | Murata | |
| 2011/0267340 A1 | 11/2011 | Kraus | |
| 2013/0222566 A1 | 8/2013 | Murase | |
| 2014/0063447 A1 | 3/2014 | Piotrowski | |
| 2014/0205169 A1 | 7/2014 | Yamakawa | |
| 2015/0092160 A1 * | 4/2015 | Chen | A61B 3/0025 351/206 |
| 2015/0116662 A1 | 4/2015 | Wada | |
| 2016/0000321 A1 | 1/2016 | Iwase | |
| 2017/0020387 A1 | 1/2017 | Fingler | |
| 2017/0127936 A1 | 5/2017 | Iwase | |
| 2017/0131082 A1 | 5/2017 | Cheng | |
| 2017/0358077 A1 * | 12/2017 | Xu | A61B 5/0066 |
| 2019/0343381 A1 * | 11/2019 | Dastmalchi | A61B 5/7445 |

* cited by examiner

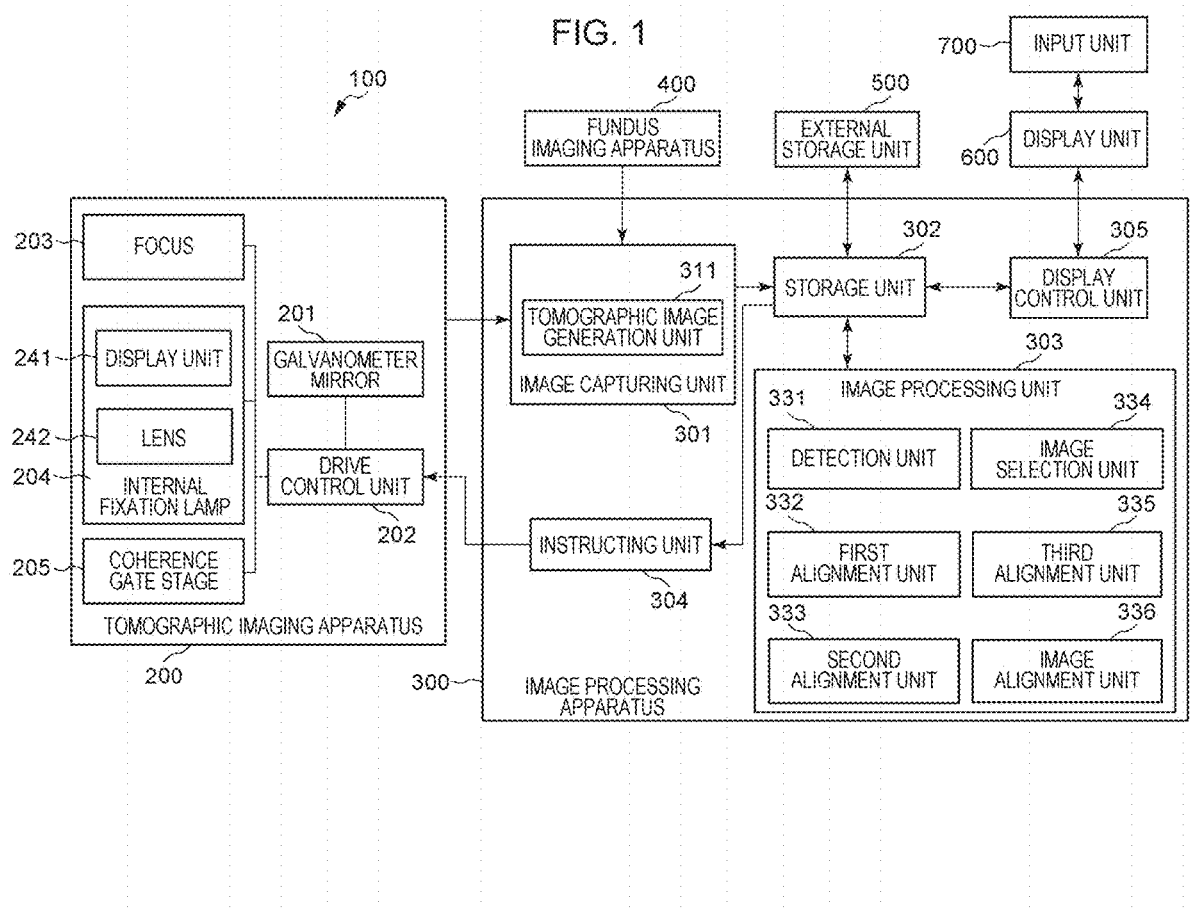

FIG. 6A
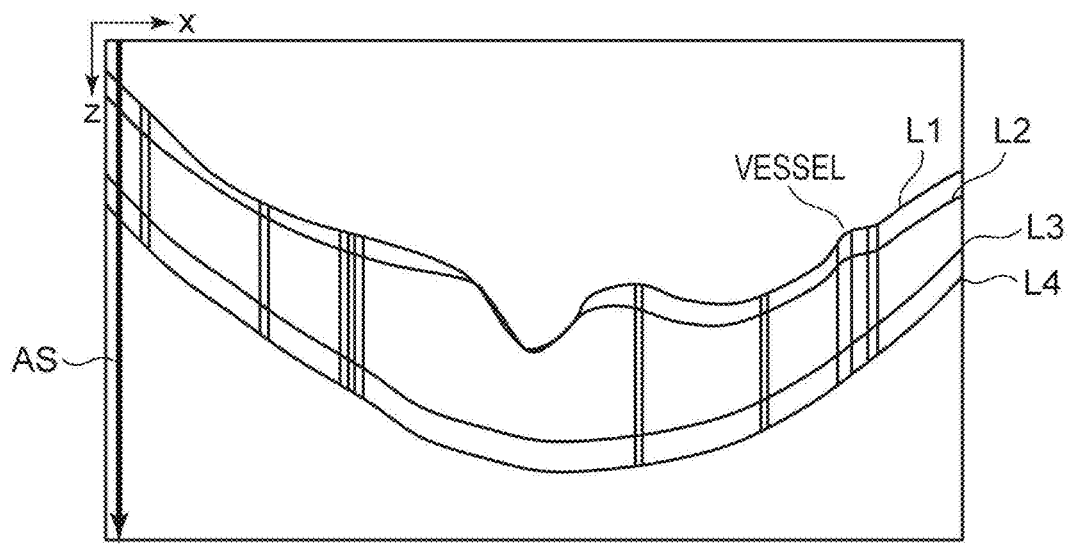
FIG. 6B
FIG. 6C
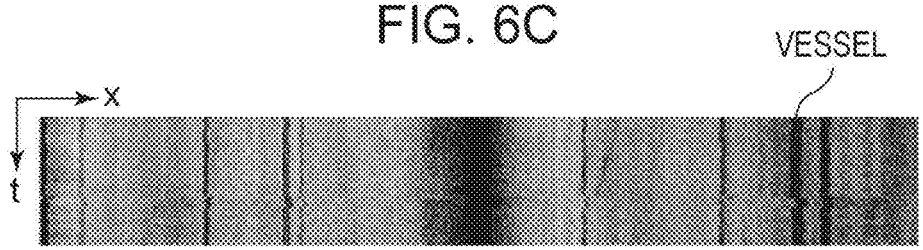

REFERENCE REFERENCE MASK

TARGET 1 TARGET MASK 1

IMAGE PROCESSING APPARATUS, ALIGNMENT METHOD AND STORAGE MEDIUM

BACKGROUND OF THE INVENTION

Field of the Invention

The disclosed technology relates to an image processing apparatus, an alignment method and a storage medium.

Description of the Related Art

An averaged image or an OCTA (OCT Angiography) image can be generated from a plurality of two-dimensional tomographic images acquired by optical coherence tomography (OCT). Because a target's eye moves, an alignment of a plurality of two-dimensional tomographic images may be required for generation of an positional difference amount. Some of alignment methods applying an image correlation between tomographic images may require more calculation amount and may be performed at a lower speed. European Patent Application Publication No. 2693397 discloses performing an alignment based on a boundary line of a retina layer detected from a tomographic image for high-speed tomographic image alignment.

SUMMARY OF THE INVENTION

An image processing apparatus according to an aspect of the present disclosure includes a first alignment unit configured to perform an alignment in a horizontal direction on a plurality of two-dimensional tomographic images according to a first method, the plurality of two-dimensional tomographic images being obtained based on measurement light controlled to scan an identical position of an eye, and a second alignment unit configured to perform an alignment in a depth direction on the plurality of two-dimensional tomographic image according to a second method that is different from the first method.

Further features of the present invention will become apparent from the following description of exemplary embodiments with reference to the attached drawings.

BRIEF DESCRIPTION OF THE DRAWINGS

FIG. 1 illustrates an example of a configuration of an image processing system.

FIGS. 6A to 6C are diagrams for explaining examples of a projected image.

DESCRIPTION OF THE EMBODIMENTS

Figure 2A:
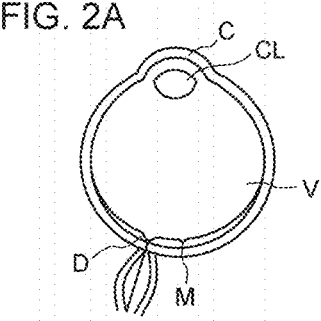
FIGS. 2A to 2C are diagrams for explaining a structure of an eye and a tomographic image and a fundus image thereof.

Such a conventional method does not consider a feature (such as a position or a disease of a blood vessel) of an inner retina because an alignment is performed based on a boundary line of a retina layer that is information regarding a retina external form. This may leave a positional deviation of a tomographic image even as a result of an accurate alignment based on a boundary line.

The embodiments described below can achieve both improved speed and accuracy of an alignment of tomographic images. Each of the embodiments of the present invention described below can be implemented solely or as a combination of a plurality of the embodiments or features thereof where necessary or where the combination of elements or features from individual embodiments in a single embodiment is beneficial.

Embodiment 1

With reference to the drawings, a first embodiment of the present disclosure will be described below. It should be noted that an image processing apparatus according to Embodiment 1 may generate two-dimensional tomographic images with reduced noise by performing alignment of a plurality of tomographic images quickly and accurately, and proper selection of an alignment reference tomographic image for averaging. Numerical values according to the following embodiments are merely given for illustration purposes, and the present disclosure is not limited by the disclosed numerical values.

According to this embodiment, even in a case where a retina layer deforms due to an involuntary eye movements during fixation within a two-dimensional tomographic image, a high quality two-dimensional tomographic image can be acquired. Here, the expression "high quality image" refers to an image with a higher S/N ratio than that resulting from one imaging operation. Alternatively, the expression "high quality image" may be an image with an increased amount of information for diagnosis.

An image processing system including the image processing apparatus according to this embodiment will be described in detail.

FIG. 1 illustrates a configuration of an image processing system 100 including an image processing apparatus 300 according to this embodiment. As illustrated in FIG. 1, the image processing system 100 is implemented by connecting the image processing apparatus 300 to a tomographic imaging apparatus (also called an optical coherence tomography or OCT) 200, a fundus imaging apparatus 400, an external storage unit 500, a display unit 600, and an input unit 700 via an interface.

The tomographic imaging apparatus 200 is an apparatus configured to capture a tomographic image of an eye. An apparatus to be used as the tomographic imaging apparatus may include an SD-OCT or an SS-OCT, for example. Because the tomographic imaging apparatus 200 is a known apparatus, any repetitive detail descriptions will be omitted.

Imaging of a tomographic image thereby in response to an instruction from the image processing apparatus 300 will be described.

Referring to FIG. 1, a galvanometer mirror 201 is configured to scan measurement light in the fundus and defines an imaging range for the fundus by the OCT. A drive control unit 202 is configured to control a driving range and a speed of the galvanometer mirror 201 to define an imaging range and a number of scanning lines in a planar direction (scanning speed in the planar direction) in the fundus. Although the galvanometer mirror is illustrated as one unit for simplicity, the galvanometer mirror in reality includes two mirrors for X scanning and Y scanning and can scan a desired range on the fundus with measurement light.

A focus 203 is configured to bring the retina layer of the fundus into focus through an anterior eye portion of a target eye. The measurement light is brought into focus to the retina layer of the fundus through the anterior eye portion of the target eye via a focus lens, not illustrated. The measurement light applied to the fundus is reflected and scattered by the retina layer.

An internal fixation lamp 204 includes a display unit 241 and a lens 242. The display unit 241 may be a plurality of light emitting diodes (LEDs) arranged in a matrix pattern. The lighting positions of the light emitting diodes are changed in accordance with an area to be imaged under control of the drive control unit 202. The light from the display unit 241 is guided to the target's eye through the lens 242. The light emitted from the display unit 241 is 520 nm long, and the drive control unit 202 displays a desired pattern.

A coherence gate stage 205 is controlled by the drive control unit 202 for addressing a difference in eye axial length of the target's eye, for example. The term "coherence gate" refers to a position at equal optical distance of measurement light and reference light in the OCT. The position of the coherence gate may be controlled according to an image capturing method for imaging on the retina layer side or a deeper part of the retina layer. Next, a structure and images of an eye to be acquired by the image processing system will be described with reference to FIGS. 2A to 2C.

FIG. 2A illustrates a schematic diagram of the eyeball. FIG. 2A illustrates a cornea C, a crystalline lens CL, a vitreous body V, a macular area (having the fovea at the center of the macula) M, and an optic disk D. The tomographic imaging apparatus 200 according to this embodiment will be described mainly in a case where a posterior fundus retina is to be imaged which includes the vitreous body, the macular area, and the optic disk. The tomographic imaging apparatus 200 can image an anterior eye portion of the cornea and crystalline lens, though it is not described herein.

Figure 2B:
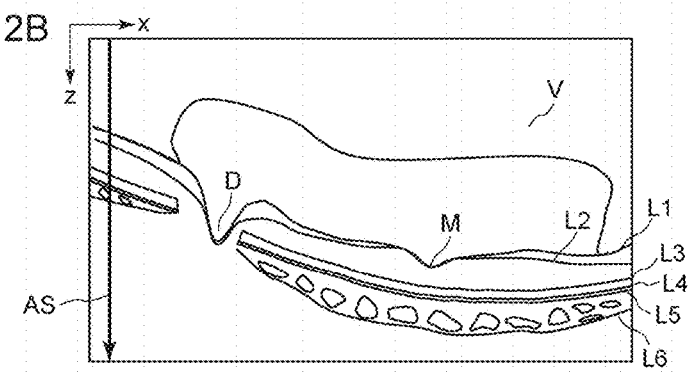

FIG. 2B illustrates an example of a tomographic image of the retina acquired by the tomographic imaging apparatus 200. FIG. 2B illustrates a unit AS for image capturing based on an A-scan of an OCT tomographic image. A plurality of A-scans configures one B-scan (in other words one B-scan includes a plurality of A-scans). The B-scan is called a tomographic image. FIG. 2B illustrates a vitreous body V, a macular area M, and an optic disk D. FIG. 2B further illustrates a boundary L1 between an inner limiting membrane (ILM) and a nerve fiber layer (NFL), a boundary L2 between a nerve fiber layer and a Ganglion cell layer (GCL), a photoreceptor inner segment outer segment (ISOS) L3, a retinal pigment epithelium (RPE) L4, a Bruch membrane (BM) L5, and a choroid L6. The tomographic image has an axis of abscissa (main-scanning direction of the OCT) as an x-axis and an axis of ordinates (vertical direction thereof) as a z axis.

Figure 2C:
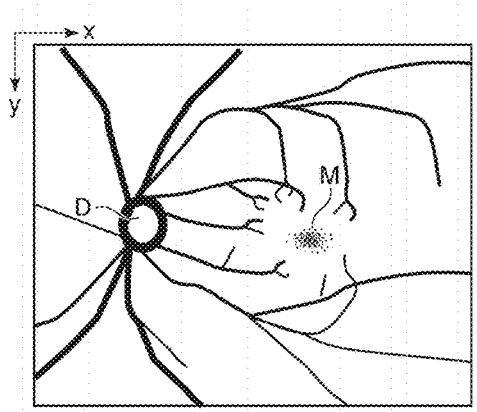

FIG. 2C illustrates a fundus image captured by the fundus imaging apparatus 400. The fundus imaging apparatus 400 is configured to capture a fundus image of the eye and may be a fundus camera or an SLO (Scanning Laser Ophthalmoscope), for example. FIG. 2C illustrates a macular area M and an optic disk D and thick lines representing blood vessels. The fundus image has an axis of abscissa (main-scanning direction of the OCT) as an x-axis and an axis of ordinates (sub-scanning direction of the OCT) as a y axis. The tomographic imaging apparatus 200 and the fundus imaging apparatus 400 may be provided integrally or separately.

The image processing apparatus 300 includes an image capturing unit 301, a storage unit 302, an image processing unit 303, an instructing unit 304, and a display control unit 305. The image capturing unit 301 includes a tomographic image generation unit 311. The image processing apparatus 300 may include one or more processors and one or more memories, not illustrated, for example. The one or more processors may execute programs stored in the one or more memories so that the one or more processors can function as the image capturing unit 301, the image processing unit 303, the instructing unit 304, and the display control unit 305. Each of the processors may be a hardware module such as a CPU and a GPU. For example, the image processing apparatus 300 obtains signal data of a tomographic image captured by the tomographic imaging apparatus 200 and performs signal processing thereon to generate a tomographic image. For example, the image capturing unit 301 acquires a plurality of two-dimensional tomographic images based on measurement light controlled for scanning an identical position of the eye target to averaging of tomographic images thereof. Fundus image data captured by the fundus imaging apparatus 400 are also acquired. The generated tomographic images and the fundus images are stored in the storage unit 302. The image processing unit 303 includes a detection unit 331, a first alignment unit 332, a second alignment unit 333, an image selection unit 334, a third alignment unit 335, and an image composition unit 336.

The detection unit 331 is configured to detect a boundary line between layers from the retina. The first alignment unit 332 is configured to perform alignment in the horizontal direction (x-axis) of the retina. The second alignment unit 333 is configured to perform alignment in the vertical direction (z-axis) of the retina. The image selection unit 334 is configured to select a reference tomographic image for an alignment from a plurality of tomographic images and to select tomographic images to be averaged. The third alignment unit 335 is configured to set a plurality of areas for an alignment in a characteristic part within a tomographic image and at the same time to perform alignment area by area in the horizontal direction (x-axis) and the vertical direction (z-axis). The image composition unit 336 is configured to average the tomographic images selected by the image selection unit 334.

The external storage unit 500 is configured to hold, in association, information regarding a target's eye (such as the name, age and sex of the patient), captured image data, imaging parameters, image analysis parameters, and parameters set by an operator.

The input unit 700 may be a mouse, a keyboard, or a touch operation display screen, and an operator can instruct the image processing apparatus 300, the tomographic imaging apparatus 200, and the fundus imaging apparatus 400 through the input unit 700.

Figure 3A:
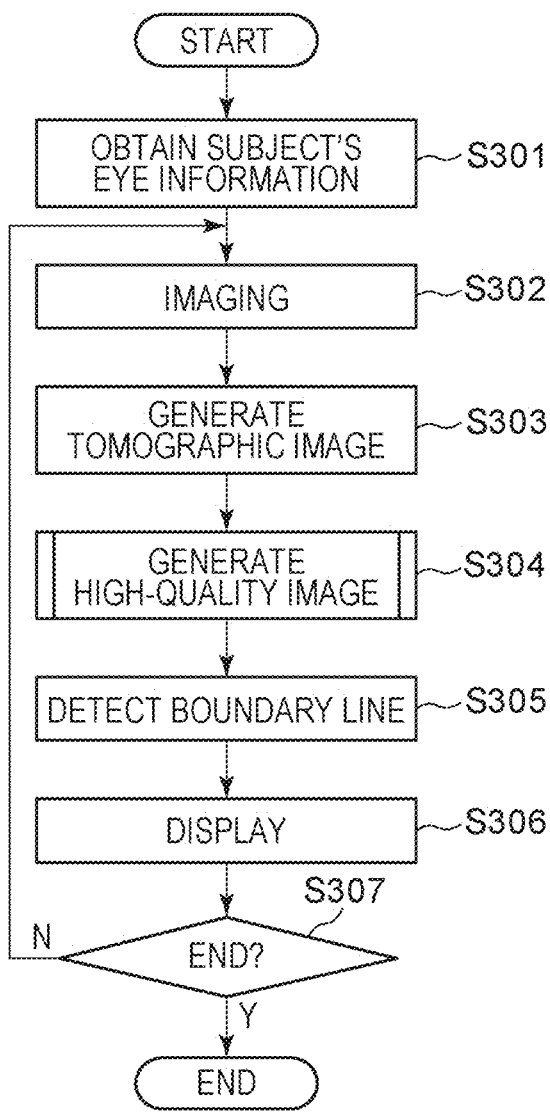
FIGS. 3A and 3B are flowcharts illustrating examples of flows of processes in the image processing system.
Figure 3B:
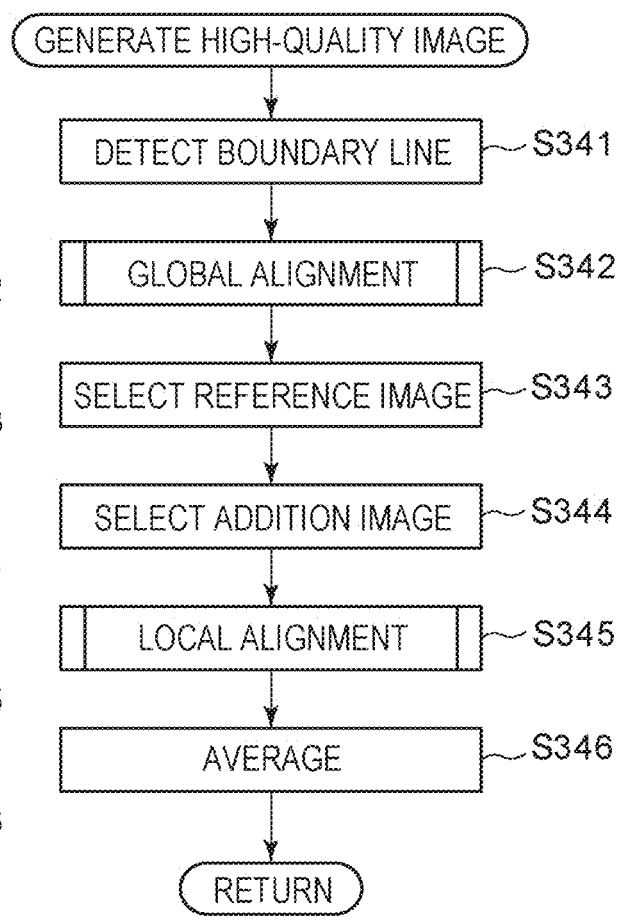
Figure 4:
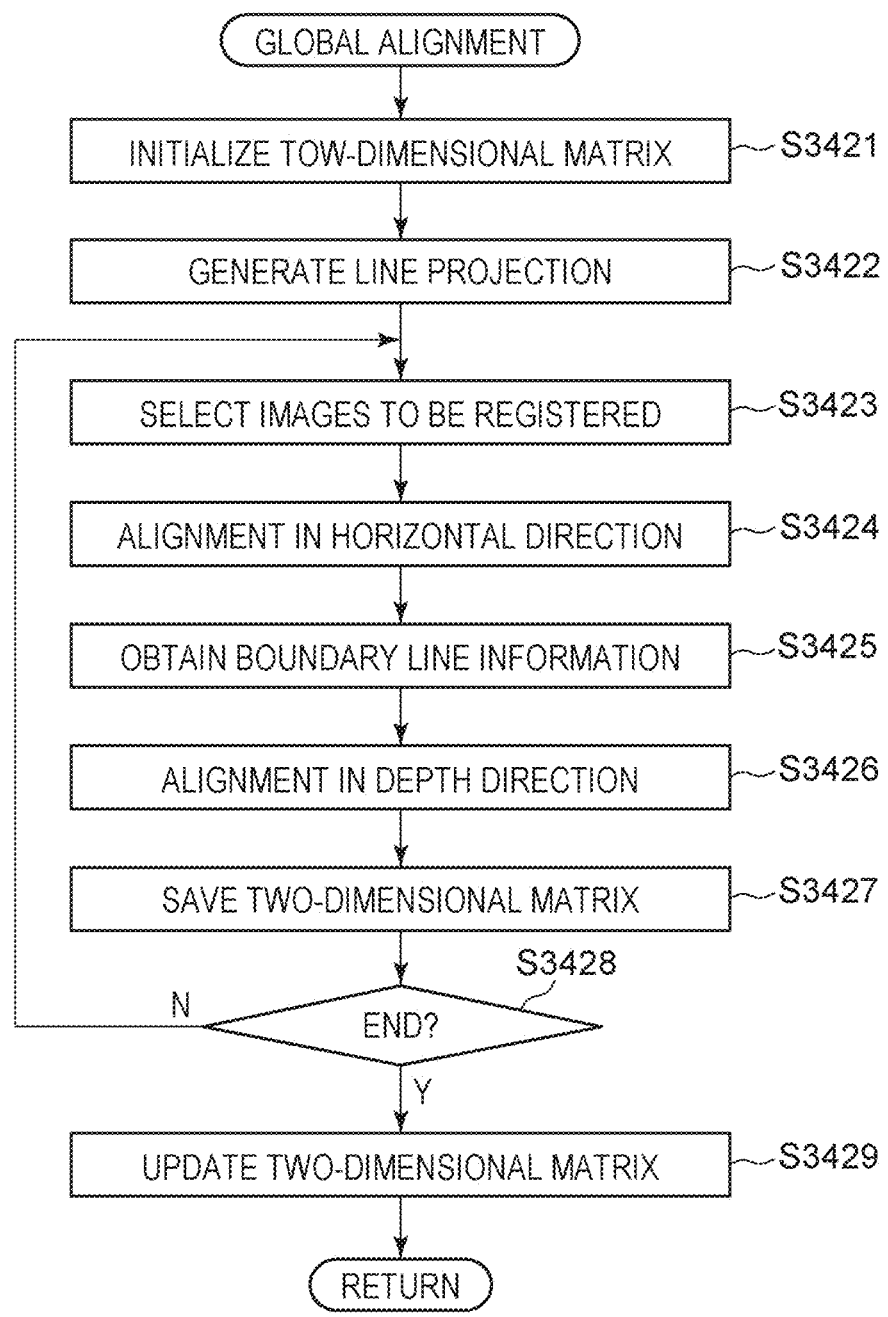
FIG. 4 is a flowchart illustrating an example of a flow of a global alignment process.
Figure 5:
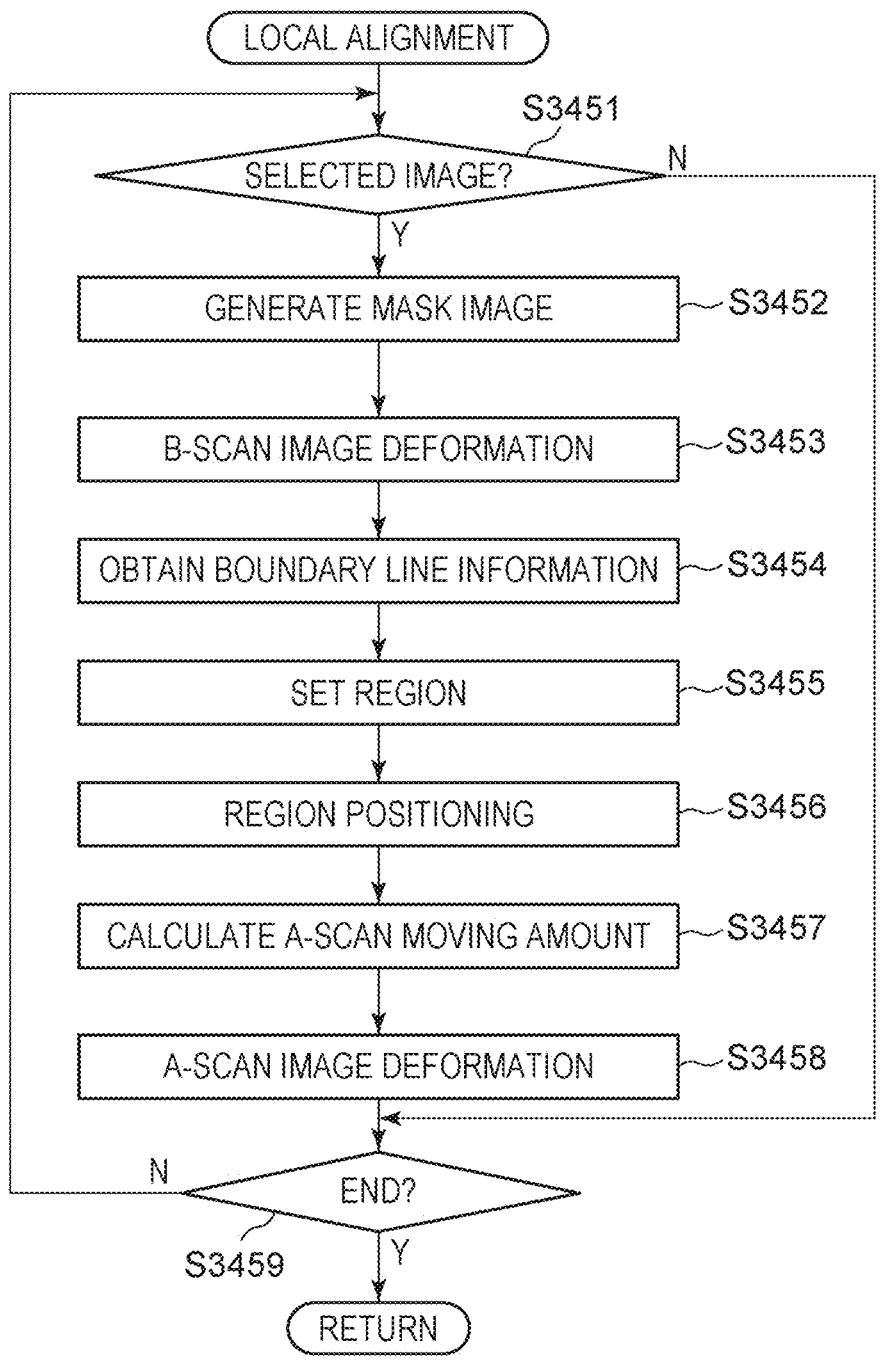
FIG. 5 is a flowchart illustrating an example of a flow of a local alignment process.

Next, with reference to FIGS. 3A and 3B, process procedures to be performed by the image processing apparatus 300 according to this embodiment will be described. FIG. 3A is a flowchart illustrating a flow of an operation process in the entire system according to this embodiment, and FIG. 3B is a flowchart illustrating a flow of a high-quality image generation process according to this embodiment.

Step S301

In step S301, a target's eye information obtaining unit, not illustrated, externally obtains a target identification number as information for identifying a target's eye. Based on the target identification number, information regarding the target's eye held in an external storage unit 500 is obtained and is stored in the storage unit 302.

Step S302

In step S302, the target's eye is scanned for imaging. In order to scan a target's eye, an operator selects a scan start, not illustrated, and the tomographic imaging apparatus 200 controls the drive control unit 202 to operate the galvanometer mirror 201 and scan a tomographic image. The galvanometer mirror 201 includes an X scanner in a horizontal direction and a Y scanner in a vertical direction. When the directions of these scanners are changed, scanning can be performed in the horizontal direction (X) and the vertical direction (Y) in an apparatus coordinate system. By changing the directions of the scanners simultaneously, scanning can be performed in a direction combining the horizontal direction and the vertical direction. Thus, scanning can be performed in an arbitrary direction on a fundus plane.

For imaging, imaging parameters are to be adjusted. More specifically, the position of the internal fixation lamp, a scan range, a scan pattern, a coherence gate position, and a focus are at least set. The drive control unit 202 controls light emitting diodes in the display unit 241 to control the position of the internal fixation lamp 204 so as to image a macular area center or an optic disk. The scan pattern defines a scan pattern such as a raster scan, a radial scan, and a cross scans for imaging a three-dimensional volume. With any of scan patterns selected, a plurality of images of one line is captured repetitively (where the number of times of repetition is two or more). According to this embodiment, a case will be described where the scan pattern is a cross scan and one identical position is to be imaged 150 times repetitively. After completion of the adjustment of the imaging parameters, an operator may select to start imaging, not illustrated, for imaging. According to the present disclosure, the tomographic imaging apparatus 200 tracks the target's eye for imaging an identical location (one line) for averaging to scan the target's eye with a reduced influence of involuntary eye movements during fixation, though the detail descriptions will be omitted.

Step S303

In step S303, a tomographic image is generated. The tomographic image generation unit 311 performs general reconstruction processing on interference signals to generate a tomographic image.

First, the tomographic image generation unit 311 performs fixed pattern noise removal from the interference signals. The fixed pattern noise removal averages a plurality of detected A-scan signals, extracts fixed pattern noise, and subtracts it from input interference signals. Next, the tomographic image generation unit 311 performs a desired window function process to optimize a depth resolution and a dynamic range having a trade-off relationship when Fourier transform is performed in a finite interval. Next, an FFT process is performed to generate a fault signal.

Step S304

In step S304, the image processing unit 303 performs composed image generation. Processing to be performed by the image processing unit 303 will be described with reference to the flowcharts in FIG. 3B, FIG. 4, and FIG. 5 and FIGS. 6A to 6C to FIGS. 13A and 13B.

Step S341

In step S341, the detection unit 331 detects a boundary line of the retina layer in the plurality of tomographic images captured by the tomographic imaging apparatus 200. The detection unit 331 detects one of boundaries L1 to L6 in the tomographic image in FIG. 2B. A median filter and a Sobel filter are applied to tomographic images to be processed to generate images (hereinafter, called a median image and a Sobel image). Next, a profile is generated for each A-scan from the generated median image and Sobel image. The median image corresponds to a luminance value profile, and the Sobel image corresponds to a gradient profile. Then, peaks are detected within the profile generated from the Sobel image. With reference to profiles of the median images before and after the detected peaks and between peaks, boundaries of the areas of the retina layer are detected.

Step S342

In step S342, between the plurality of tomographic images, an alignment in the horizontal direction (x-axis) of the retina and an alignment in the depth direction (z-axis) of the retina are performed thereon. It should be noted that the alignments here will be described as global alignment. A method for the global alignment in S342 will be described with reference to the flowchart in FIG. 4.

Step S3421

In step S3421, a two-dimensional matrix is initialized which is for storing alignment parameters for performing alignments on the tomographic images. Each matrix has elements each storing information for increased image quality such as deformation parameters and image similarities for alignments.

Step S3422

In step S3422, the first alignment unit 332 generates a line projected image. The line projected image is an example of a projected image. The line projected image and a generation method thereof will be described with reference to FIGS. 6A and 6B. FIG. 6A illustrates a schematic diagram of one tomographic image. The tomographic image has boundary lines L1 to L4, an A-scan AS, and VESSEL indicating a blood vessel. Referring to FIG. 6A, the blood vessel is indicated by an area enclosed by two vertical lines, and a deep layer part is shaded by the blood vessel in a shallow layer part. The term "line projected image" refers to an image acquired by averaging tomographic images in the z-axis direction in A-scans. FIG. 6B illustrates a schematic diagram of a line projected image generated from one tomographic image. According to this embodiment, a plurality of tomographic images of an identical position is captured for high-quality processing by using the plurality of tomographic images. FIG. 6C illustrates an example of a line projected image generated from tomographic images acquired by imaging an identical a plurality of number of times. FIG. 6C has an axis of abscissa corresponding to the X-axis of a tomographic image and an axis of ordinates corresponding to a time axis indicated by t. A tomographic image has a lower luminance value in a lower part of the blood vessel because of its shadow, compared with surrounding parts. Accordingly, the line projected image has a lower luminance value corresponding to the blood vessel.
Step S3423

In step S3423, alignment targets are selected. According to this embodiment, all tomographic images are set as reference images, and alignments are performed between the set reference tomographic images and the remaining tomographic images. Accordingly, in step S3423, a tomographic image with Index 0 is set as a reference, and alignments are performed between Index 0 and Indices 1 to 149. Next, alignments are performed between a reference tomographic image with Index 1 and Indices 2 to 149. Next, alignments are performed between a reference tomographic image with Index 2 and Indices 3 to 149. These processes are repeated. The repetition is judged in step S3428, which will be described below.

When the index of the reference image is moved up by one, the start index of the images being an alignment target is also moved up by one. This will be described with reference to a case where a tomographic image with Index 2 is set as a reference image. When Index 2 is set as a reference, the alignment between Index 0 and Index 1, Index 0 and Index 2, and Index 1 and Index 2 have already undergone an alignment by the processes up to that point. Therefore, when a tomographic image with Index 2 is set as a reference, an alignment may start from Index 3. Thus, for alignments between all tomographic images, half combinations thereof may be calculated.
Step S3424

Figure 7A:
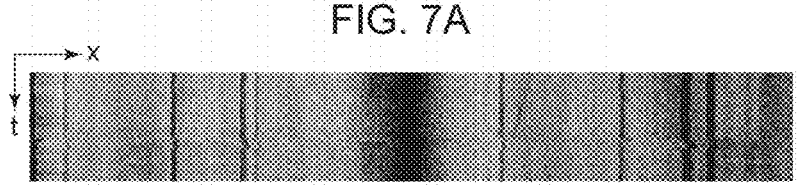
FIGS. 7A and 7B are diagrams for explaining an example of a line projected image alignment.
Figure 7B:
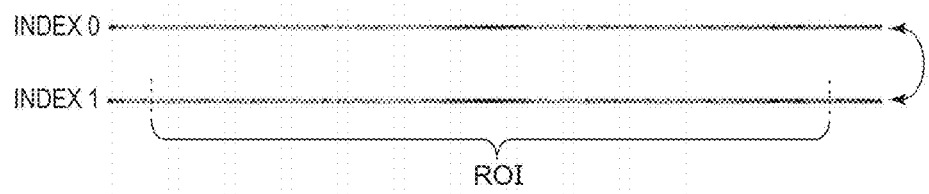

In step S3424, the first alignment unit 332 performs an alignment in a horizontal direction (x-axis) on the retina between the plurality of tomographic images. Here, the alignment in the horizontal direction applies line projected images generated in step S3422. The alignment applying line projected images corresponds to an example of an alignment according to a first method. The line projected image alignments will be described with reference to FIGS. 7A and 7B. FIG. 7A illustrates an example of a line projected image generated from tomographic image group acquired by a plurality of imaging operations performed on an identical position. Referring to FIG. 7A, focusing on a blood vessel part, a slight difference may be found as a result of tracking of the target's eye during an imaging operation. Accordingly, the positional difference is to be corrected. Although image data is used here, image data targets for alignments are one-dimensional data, as illustration in FIG. 7B. FIG. 7B illustrates line projected images Index 0 and Index 1 having an image size of 1024×1. With reference to Index 0, an image of a range of ROI of Index 1 undergoes an alignment. The ROI has a size smaller than the image size in the horizontal direction and has an equal size in the vertical direction. For example, the ROI may have a size of 1000×1. The alignment processing to be performed between images may include, for example, pre-defining an evaluation function representing a similarity between two line projected images, calculating the evaluation value for changed line projected image positions, and determining a location having the highest evaluation value as an alignment result. In other words, a moving amount to a location having the highest evaluation value is defined as a positional deviation amount between the line projected images for performing an alignment. The evaluation function may be a method for evaluating a pixel value (such as a method for evaluating by using a correlation coefficient).

Expression 1 is an expression in a case where a correlation coefficient is used as an evaluation function representing a similarity.

$$\frac{\iint_S (f(x,z) - \bar{f})(g(x,z) - \bar{g})dxdz}{\sqrt{\iint_S (f(x,z) - \bar{f})^2 dxdz \iint_S (g(x,z) - \bar{g})^2 dxdz}} \quad \text{[Expression 1]}$$

In Expression 1, f(x,z) is an area of a first line projected image, and g(x,z) is an area of a second line projected image.

$$\bar{f}, \bar{g} \quad \text{[Expression 2]}$$

represents an average of the areas f(x,z) and the area g(x,z). The term "area" here refers to an image area to be used for an alignment, and the area has a size equal to or smaller than that of a normal line projected image and is set as an ROI size as described above.

The evaluation function is not limited to the one described above but may be a SSD (Sum of Squared Difference) or a SAD (Sum of Absolute Difference) for evaluating a similarity or a difference between images.

Alternatively, the alignment may be performed based on a method such as POC (Phase Only Correlation).

Because an alignment is performed between line projected images, the image alignment is performed one-dimensionally and can be performed in a horizontal direction in a quick and stable manner. Information indicating whether there are similar image features or not can be calculated.
Step S3425

In step S3425, the boundary line information detected in step S341 is obtained. The boundary line to be obtained here may be boundary line information on tomographic images that are current alignment targets. For example, boundary line information between Index 0 and Index 1 may be obtained.
Step S3426

Figure 8A:
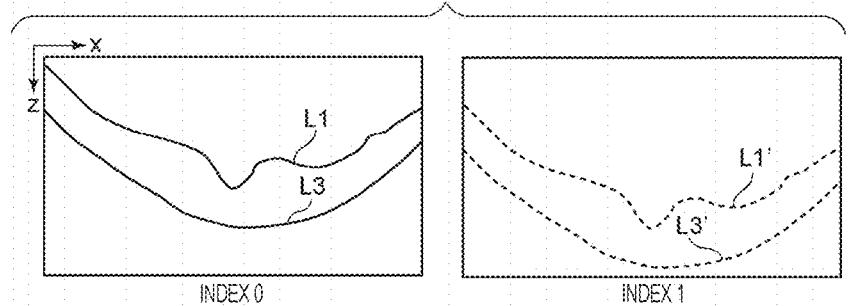
FIGS. 8A to 8C are diagrams for explaining an example of a boundary line alignment.

In step S3426, the second alignment unit 333 performs an alignment in a depth direction (z-axis) on the retina. Here, the boundary line information is used for an alignment in the depth direction. The alignment applying boundary information corresponds to an example of an alignment according to a second method to be executed at a different clock time from that of the alignment according to the first method. The boundary line information alignment will be described with reference to FIGS. 8A to 8C. FIG. 8A illustrates an example of a boundary line to be used for an alignment. According to this embodiment, a boundary line L1 (ILM) and a boundary line L3 (ISOS) are used.

FIG. 8A illustrates a reference image Index 0 and a target image Index 1. The reference image and the target image undergo an alignment in a horizontal direction in step S3424. Accordingly, an alignment in a depth direction by using the reference boundary lines L1, L3 and alignment target boundary lines L1', L3' corrected with a horizontal alignment parameter are used for an alignment in the depth direction. It should be noted that the layer boundary to be used for an alignment is not limited to the layer boundary as described above, and the number of layer boundaries to be used is not limited to two. The alignment using the boundary information corresponds to an example of the alignment according to the second method to be executed at a different clock time from that of the alignment according to the first method.

Figure 8B:
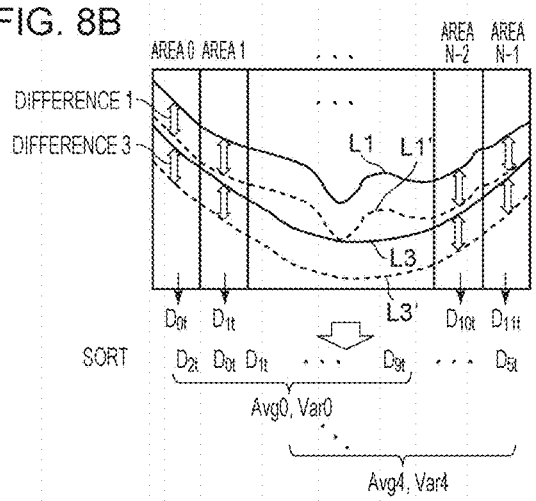

Referring to FIG. 8B, the reference image boundary lines L1, L3 and the alignment target boundary lines L1', L3' are displayed simultaneously for simple description. Referring to FIG. 8B, the boundary lines are divided into N in the vertical direction. This results in Area 0 to Area N−1. Referring to FIG. 8B, the entire image is actually divided into areas though the image at the center is not divided for clear illustration. A vertical arrow Difference 1 represents a difference (positional deviation amount) between L1 and L1', and a vertical arrow Difference 3 represents a difference between L3 and L3'. These differences are acquired for each of the Area 0 to Area N−1. Although, for simplicity, the boundary lines in the horizontal direction have an equal size according to this embodiment, the retina layer in reality may deviate upward (in the direction O of the z-axis) in an image, and a partial area of the retina layer may be missing from the image. In this case, a boundary line cannot be detected in the entire image. Accordingly, a range in which boundary lines between the reference image boundary lines L1, L3 and the alignment target boundary lines L1', L3' may be divided into N for alignment between the boundary lines. The following description assumes that the number N of divisions is equal to 12. The number N of divisions may be changed in accordance with the image size in the horizontal direction. Alternatively, the number N of divisions may be changed in accordance with the size of the horizontal width of a commonly detected boundary line.

FIG. 8B illustrates averages $D_{0t}$ to $D_{11t}$ of Difference 1 and Difference 3 in each of the areas. In other words, the average of differences between ILM and ISOS is handled as a representative value of the differences in the area. Next, the representative values $D_{0t}$ to $D_{11t}$ acquired in each of the areas are sorted in increasing order. M representative values in increasing order of the sorted representative value are used to calculate an average and a variance. The following description according to this embodiment assumes that M is equal to 8. However, the number is not limited thereto. The number of Ms may be lower than the number of Ns (M<N). The average and the variance are calculated by shifting the sorted representative values by one. In other words, according to this embodiment, because eight representative values of 12 divided areas are used for the calculation, five average values and five variance values can be acquired in total. Next, an average value corresponding to the minimum variance value among the five variance values is defined as a shift value in the depth direction. For example, in a case where the minimum variance value is Var0 among five variance values, the shift value in the depth direction is Avg0. In this manner, an area for boundary line alignment may be divided, and a value producing a minimum variation among combinations of difference values of the divide areas may be used, which prevents use of areas causing improper boundary line detection. Therefore, the shift value in the depth direction can be calculated in a stable manner. Having described that an average value is used as the shift value in the depth direction, a median value may be used instead. In other words, a representative value may be used. Furthermore, having described a variance value is used as a value indicative of a variation, a standard deviation or an index which can evaluate a variation of a value can be used. Having described the example that the representative values are sorted in increasing order, the representative values may be sorted in decreasing order. The second alignment unit 333 in this way is configured to sort positional deviation amounts of a plurality of areas in order based on the values of the positional deviation amounts, sequentially select a predetermined number of combinations of positional deviation amounts in increasing or decreasing order, calculate values indicative of variations of the combinations, and select a combination of positional deviation amounts having a minimum variation value.

Figure 8C:
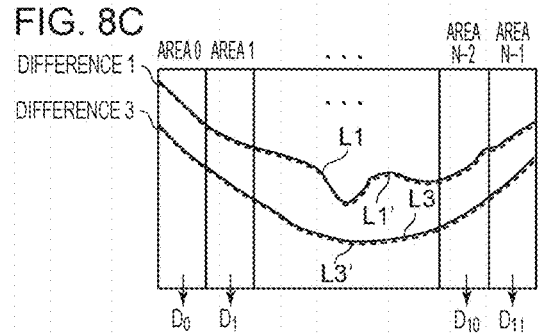

Finally, the acquired shift value in the depth direction is used to shift the entire boundary lines in the Z direction. FIG. 8C illustrates the example. Again, difference values in the Area 0 to Area N−1 are calculated. Representative values $D_0$ to $D_{11}$ of the difference values acquired in the areas are sorted in increasing order. M of sorted representative values are used from the lowest value to calculate an average value. The average value will be called global Distance. Thus, a final positional deviation amount (global Distance) between the boundary lines after alignment of the reference image and the target image in the X direction and the Z direction is determined.

The number N of divisions and the number M of selections for calculating a shift value in the depth direction are assumed to be equal to numbers N and M of divisions for calculating the final positional deviation amount (global Distance) in the description above. However, embodiments of the present disclosure are not limited thereto. These numbers may be different or identical. For example, the number N of divisions for calculating the shift value may be equal to 12, the number M of selections may be equal to 8, the number N of divisions for calculating a positional deviation amount (global Distance) may be equal to 15, and the number M of selections may be equal to 10.

Referring to FIG. 8C, the boundary lines are shifted for simple illustration. However, data may not actually be shifted, but the difference value of each area may be calculated in consideration of the shift value in the depth direction.

Step S3427

In step S3427, values for alignment and image similarity initialized in step S3421 are stored in a two-dimensional matrix for storing parameters for higher image quality. For example, in a case where a reference image has Index 0 and a target image has Index 1, an alignment parameter X in the horizontal direction, an alignment parameter Z in the depth direction, representative values $D_0$ to $D_{11}$ of difference values of areas, global Distances and image similarities are stored in an element (0, 1) of a two-dimensional matrix. In addition to these kinds of information a false flag as a result of a boundary line detection may be stored in association with a darker image having a boundary line that is detected clearly due to a blink. On the other hand, if the layer boundary detection succeeds, a true flag may be stored in association with the image. In a case where the boundary line alignment includes alignment by rotating a boundary line itself, the turn angle and the center coordinates of the rotation axis may further be stored, details of which will not be described in this description of this embodiment. A magnification may further be store if a magnification correction is to be corrected.

Step S3428

In step S3428, whether alignment has been performed on all images with the remaining target image being a reference image or not is determined. If all images are not processed as the reference images, the processing returns to step S3423. If so, the processing moves to step S3429.

Step S3429

In step S3429, the remaining elements of the two-dimensional matrix are updated. The process above calculates half of the combinations as in step S3423. For that reason, those values are copied to the elements that have not been calculated. For example, parameters in an element (0, 1) in the two-dimensional matrix are copied to an element at (1, 0). In other words, an element (i, j) is copied to an element (j, i). In this case, because the alignment parameters X and Z and the turn angle are reversed, they are copied after being multiplied by a negative value. Because an image similarity, for example, is not reversed, the same value is copied as it is.

These processes are performed in the global alignment. In the flow above, a Z-direction alignment is performed after an X-direction alignment, but an X-direction alignment may be performed after a Z-direction alignment. Alternatively, a Z-direction alignment may be performed after an X-direction alignment, and, again, a Z-direction alignment may be performed after an X-direction alignment. In this manner, alignments may be repeated several times. The process flow now returns to FIG. 3B.

Step S343

In step S343, the image selection unit 334 selects a reference image. The reference image selection is performed based on a result of the global alignment performed in step S342. In step S342, a two-dimensional matrix is generated, and information for generating a high quality image is stored in elements of the matrix. Thus, the information is used to perform the reference image selection. In the reference image selection, in a case where a boundary line detection flag is stored, the information is used, and the image similarity (that is an example of a result of a comparison between projected images) acquired in the horizontal direction alignment and representative values $D_0$ to $D_{11}$ of the difference values of the areas acquired in the depth direction alignment. More specifically, images with Index 0 are counted within a range of elements (0, 0) to (0, 149) in the two-dimensional matrix, having True as a boundary line detection flag, having an image similarity equal to or higher than a threshold value, and having representative values $D_0$ to $D_{11}$ of the difference value acquired for the areas within a threshold value (or equal to or lower than the predetermined threshold value) in eight or more areas of 12 areas. Also, images with Index 1 are counted within a range of elements (1, 0) to (1, 149) in the two-dimensional matrix, having True as a boundary line detection flag, having an image similarity equal to or higher than a threshold value, and having representative values $D_0$ to $D_{11}$ of the difference value acquired for the areas within a threshold value in eight or more areas of 12 areas. These processes are performed on all of the images. It should be noted that one of the image similarities acquired in the horizontal direction alignment and representative values $D_0$ to $D_{11}$ of the difference values acquired for the areas in the depth direction alignment may be used.

Figure 9A:
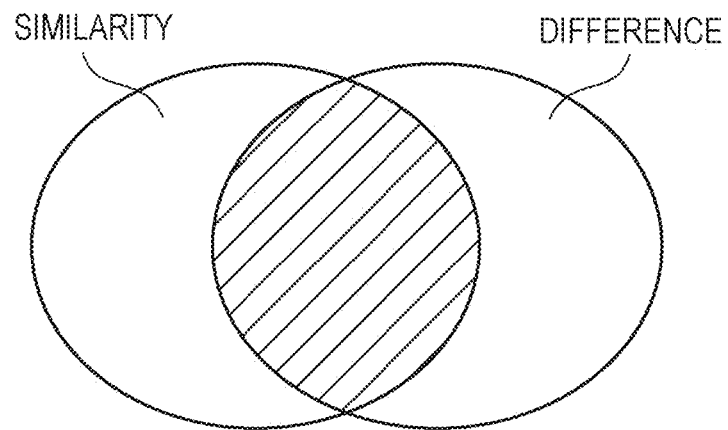
FIGS. 9A and 9B are diagrams for explaining an example of a reference image selection.
Figure 9B:
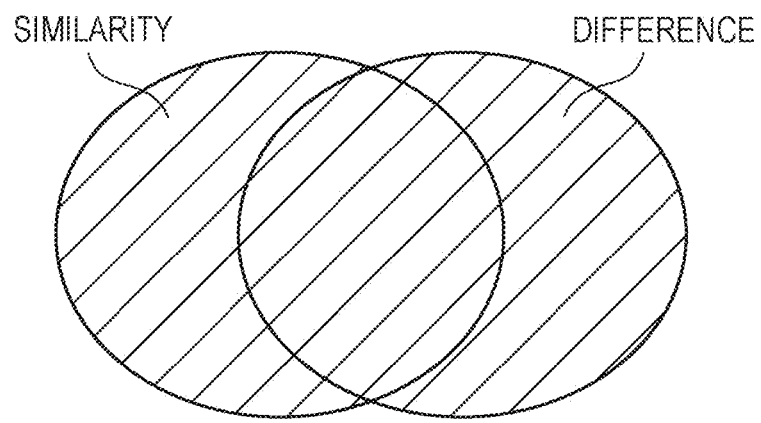

Next, examples will be described with reference to FIGS. 9A and 9B in which the conditions of the image similarities and the representative values $D_0$ to $D_{11}$ of the difference value acquired for the areas are satisfied. FIG. 9A illustrates an example in which the conditions of the image similarities and the representative values $D_0$ to $D_{11}$ of the difference values acquired for areas being equal to or lower than a threshold value in eight or more areas of 12 areas are simultaneously satisfied, which is shaded in FIG. 9A. FIG. 9B illustrates a total of the number satisfying the condition of the image similarities and the number satisfying the condition that the representative values $D_0$ to $D_{11}$ of the difference values acquired for areas being equal to or lower than a threshold value in eight or more areas of 12 areas, which is shaded in FIG. 9B. According to this embodiment, both of the conditions are simultaneously satisfied as illustrated in FIG. 9A. However, embodiments of the present disclosure are not limited thereto. As illustrated in FIG. 9B, each of conditions may be independently satisfied, and the total of the numbers may be counted. The reference image selection is not limited to the numerical values of eight or more areas of 12 areas but may be based on other numerical values.

Then, tomographic images the number of which is at a maximum under the conditions are selected as reference images. In other words, in a case where the image selection unit 334 compares, among of a plurality of two-dimensional tomographic images, one two-dimensional tomographic image and a plurality of other two-dimensional tomographic images, the image selection unit 334 selects reference images based on the number of two-dimensional tomographic images having similarities equal to or higher than a predetermined threshold value and having positional deviation amounts of layer boundaries equal to or lower than a predetermined threshold value. More specifically, the image selection unit 334 selects reference images based on, in a case where one two-dimensional tomographic image and a plurality of other two-dimensional tomographic images are compared among a plurality of two-dimensional tomographic images, the number of two-dimensional tomographic images having similarities equal to or higher than a predetermined threshold value and the number of areas equal to or higher than a predetermined number where the areas are a plurality of areas dividing the two-dimensional tomographic images in the horizontal direction having positional deviation amounts of layer boundaries equal to or lower than a predetermined threshold value.

It should be noted that in a case where there are images having an equal number satisfying the conditions, a reference image may be selected based on another evaluation value such as one with an image similarity having a highest total or average value, one with a highest total number of difference values with their representative values $D_0$ to $D_{11}$ acquired for each of the areas equal to or lower than a threshold value, one with a lowest total value or average value of global Distance, one with a detected boundary line having a maximum length or one with a boundary line in the depth direction positioned closer to the center. One or a plurality of these conditions may be applied. They may be used not only as a criteria for narrowing in a case where there are the images having an equal count satisfying the conditions but also for counting images satisfying the conditions for the reference image selection.

Step S344

In step S344, the image selection unit 334 may select an addition image. The addition image selection includes judging whether another image satisfies a condition with respect to the reference image acquired in step S343. For addition image selection, an image selection flag may be set, and if a condition is satisfied, True is set thereon, and if not, False is set thereon. As conditions for the addition image selection, the number of images having True as the boundary line detection flag, an image similarity equal to or higher than a threshold value, and having representative values $D_0$ to $D_{11}$ of difference values of the areas within a threshold value equal to or more than eight areas of 12 areas, for example, like step S343. It should be noted that different threshold values may be applied between the addition image selection and the reference image selection. For example, a tight threshold value condition may be applied for the reference image selection while a looser condition may be applied for the addition image selection than that for the reference image selection. Alternatively, an equal condition may be used for the reference image selection and the addition image selection.

Figure 10A:
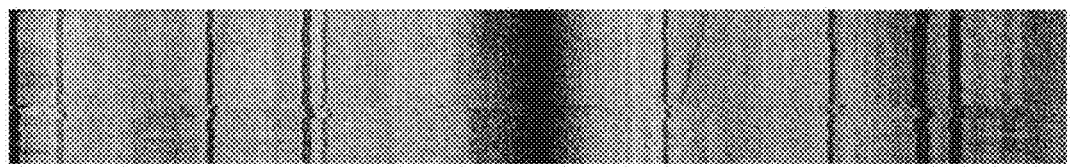
FIGS. 10A to 10C are diagrams for explaining alignment and image selection.
Figure 10B:
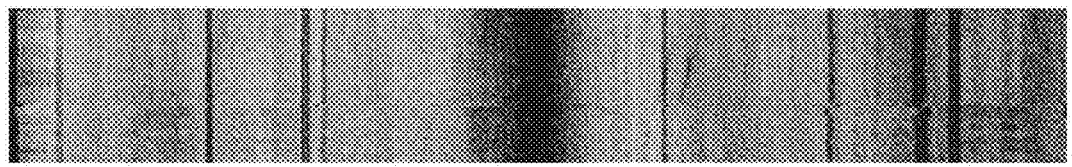
Figure 10C:
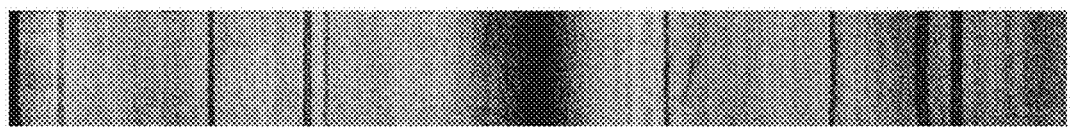

FIGS. 10A to 10C illustrate examples of line projected images generated by using tomographic images selected after alignment by the first alignment unit 332, the second alignment unit 333, and the image selection unit 334. FIG. 10A illustrates a line projected image generated from a tomographic image before an alignment, FIG. 10B illustrates a line projected image generated from a tomographic image after an alignment, and FIG. 10C illustrates a line projected image generated by using a tomographic image selected after an alignment. Focusing on a feature of the blood vessel, FIG. 10B has more linearly uniform blood vessels than that of the FIG. 10A. Referring to FIG. 10C, a part having a locally deviated blood vessel is excluded, and an image acquired by capturing a substantially identical position is only selected.

Step S345

In step S345, the third alignment unit 335 sets a plurality of areas for alignment in a part having a tomographic image internal feature between a reference image and a plurality of selected tomographic images, and alignments in the horizontal direction (x-axis) and in the depth direction (z-axis) are simultaneously performed on the retina in areas. The alignments here will be described as local alignments. A method to be applied in the local alignment in S345 to be performed by the third alignment unit 335 will be described with reference to the flowchart in FIG. 5.

Step S3451

In step S3451, a process to be performed is determined based on whether a given image has already been selected in step S344 or not. If the image selection flag has True, the processing moves to step S3452. If the image selection flag has False, the processing moves to step S3459.

Step S3452

In step S3452, a mask image is generated for an averaging process. The mask image, for example, may have all pixels having a value of 1.0. According to this embodiment, all values are equal. However, embodiments of the present disclosure are not limited to use of a mask image. Weighting may also be performed in accordance with a location. For example, vertical and horizontal peripheral areas (about several pixels) of an image may have a value lower than 1.0. In this case, the values may not be lowered uniformly, but the value may be lowered gradually as they go from the center to ends of the image.

Step S3453

Figure 11A:
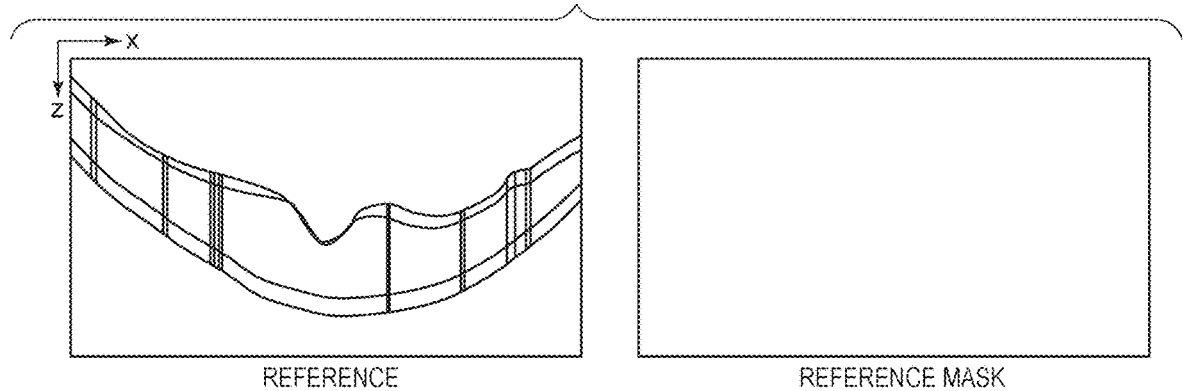
FIGS. 11A and 11B are diagrams for explaining an example of image deformation by global alignment.
Figure 11B:
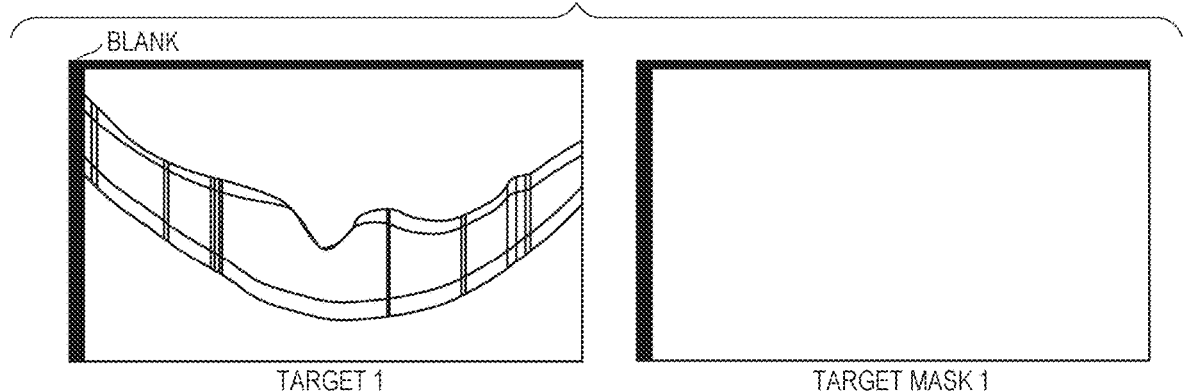

In step S3453, image deformation is performed in tomographic images (B-scans). This will be described with reference to FIGS. 11A and 11B. FIG. 11A illustrates examples of a reference image and a reference mask image, and FIG. 11B illustrates a target image 1 and target mask image 1 acquired by shifting the images in FIG. 11A to the lower right direction. As illustrated in FIGS. 11A and 11B, tomographic images excluding the reference image are deformed based on the alignment parameters X and Z acquired by the global alignment in step S342. The black areas illustrated in FIG. 11B are invalid areas caused by the shift of the images in the X and Z directions as a result of the alignments. Here, because no image data are present, the value is equal to 0. Not only the tomographic image but also the mask image is deformed with the same parameter.

Step S3454

In step S3454, the boundary line information detected in step S341 is obtained. It should be noted that the boundary line to be obtained here is boundary line information only of the current alignment reference tomographic image. According to this embodiment, the boundary lines L1 and L3 are acquired.

Step S3455

In step S3455, an alignment area is set such that it includes a feature area of the target image. This will be described with reference to FIG. 12.

Figure 12:
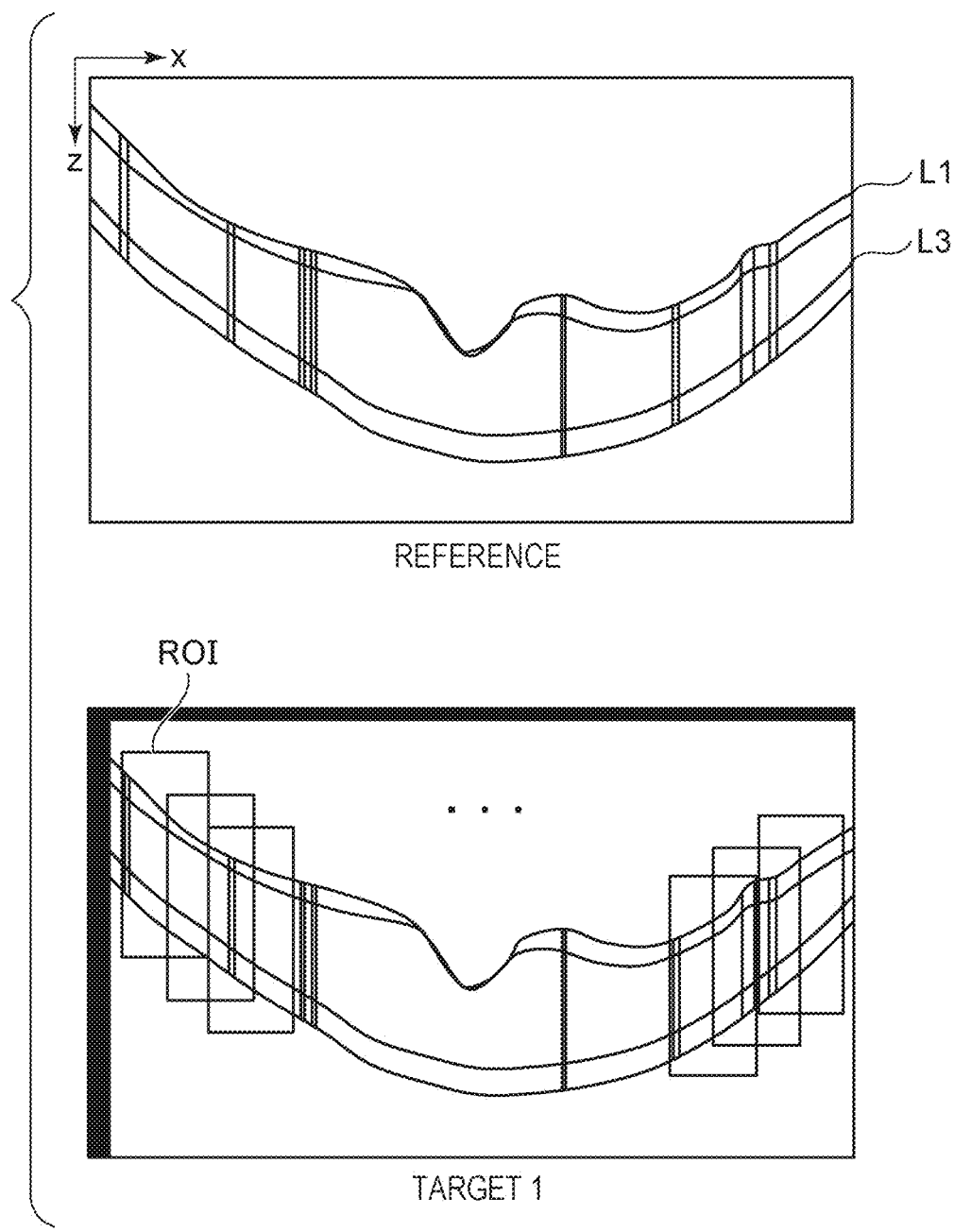
FIG. 12 illustrates diagrams for explaining an example of local alignment.

FIG. 12 illustrates a reference image and a target image 1. The target image 1 has a plurality of alignment areas (or ROIs (regions of interest)) set based on the boundary line information L1 and L3 of the reference tomographic image. The size in the depth direction of the ROI is set wider in the upper and lower directions by about several 10 pixels with reference to the lines L1 and L3. In a case where parameters of about several 10 pixels in the upward and lower directions are set, the result of the global alignment may be used to correct the parameter. In a case where the entire image is shifted toward the lower direction in the global alignment as illustrated in the target image 1 in FIG. 12, there is an invalid area in an upper end part of the image. In this case, the initial size of the ROI may be corrected so as not to include the range for setting the ROI and a search area therefor. The size in the horizontal direction of the ROI is set from a size dividing the image into K. The number K of divisions is set in accordance with an imaging parameter such as the size of the image (the number of A-scans) or the size of image capturing (10 mm). For example, according to this embodiment, in a case where the number of A-scans is equal to 1024 and the size of image capturing is equal to 10 mm, the number K of divisions is equal to 10. The set values for the size in the horizontal direction and for an ROI are also corrected by using the result of the global alignment. Because there may be an invalid area in the horizontal direction, like the parameters in the vertical direction, a range for setting the ROI and a search area therefor may be set so as not to include the invalid area.

The ROIs for a local alignment are set to superimpose on each other. This is because when ROIs are not overlapped and the size of the resulting ROI is small, there may be a location in the ROI which does not include a characteristic area. For example, when the retina is imaged with a narrow angle of view (about 3 mm), the captured image may have flat tissue in a wide range. On the other hand, in a case where ROIs are not overlapped and the range of the resulting ROI is set wider to include a feature, a smaller number of samples are obtained for a local alignment, which results in a rough alignment. In order to solve these problems, the size in the X direction of the ROI is increased, and ROIs are superimposed on each other for setting. Although FIG. 12 does not render an ROI at the center of the image, an ROI is actually set on the retina from the left end to the right end of the image. The intervals for setting ROIs may be determined in consideration of a search range for an ROI alignment. More specifically, in a case where a horizontal search range for ROI alignment is XR, the interval between center coordinates of neighboring ROIs is set to be equal to or longer than 2XR. This is because there is a possibility that the center positions of the neighboring ROIs may change place with other if the interval between the center coordinates is shorter than 2XR. In this way, the positional relationship in the horizontal direction between a plurality of ROIs (first area and second area) is set based on a search range for an ROI alignment.

Step S3456

In step S3456, an ROI is used for an area alignment. The area alignment is performed on images. Accordingly, Expression 1, like the line projected image alignment in step S3424, is used for performing an alignment based on an image similarity. However, the evaluation value regarding a similarity is not limited thereto, but an SSD (Sum of Squared Difference), an SAD (Sum of Absolute Difference) or the like may be used. Alternatively, an alignment may be performed based on a method such as POC (Phase Only Correlation).

An image alignment searches whether an ROI set in a target image is located in a reference image. In this case, because the result of the global alignment performed in step S342 is used to deform the tomographic image in step S3453, the reference image and the target image are substantially in alignment. Thus, in the search range for alignment of a reference image, a search may be performed from the initial position of an ROI by the vertical and horizontal several pixels. Then, the location having the most similar pixels is determined as an alignment result. Weighting in accordance with a location may be performed in calculation of evaluation values for similarities for local alignment. In this case, the center of the search range may be most highly weighted (such as a weight of 1.0), and the weight may be reduced (such as a weight of 0.9) as the distance to the outside of the search range increases. Such a weight may be changed pixel by pixel smoothly. Thus, when there is a slight difference between evaluation values, the initial position is selected.

The search range in an ROI may be fixed or may be varied in accordance with the imaging angle of view, the region to be imaged, or an image location (end or center).

Step S3457

Figure 13A:
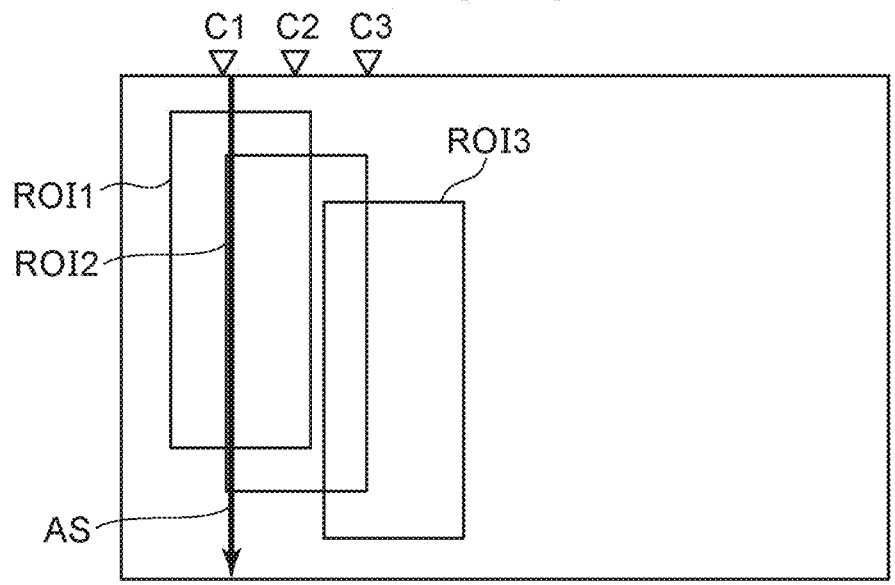
FIGS. 13A and 13B are diagrams for explaining an example of local alignment.
Figure 13B:
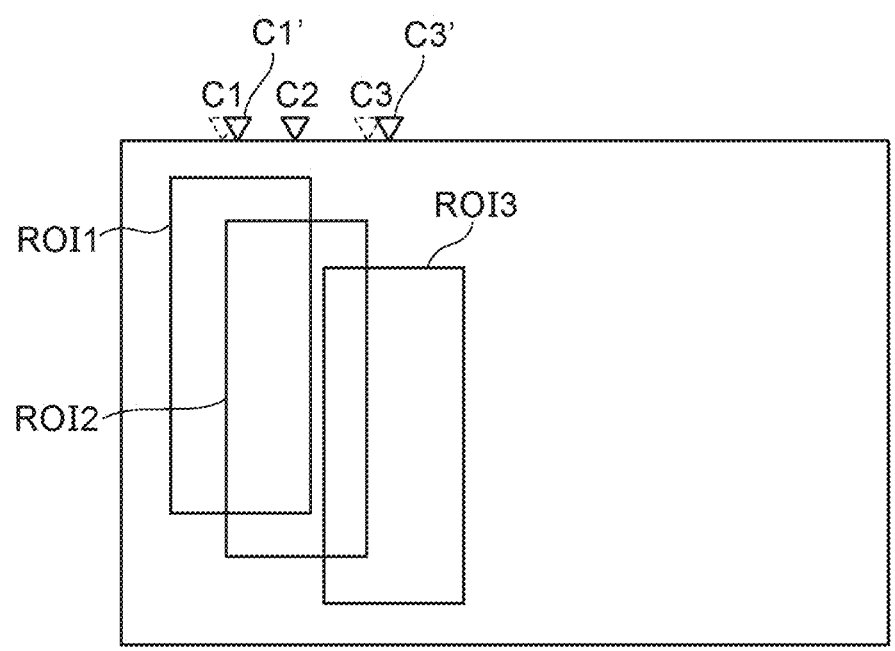

In step S3457, alignment parameters acquired in step S3456 are interpolated. This will be described with reference to FIGS. 13A and 13B. FIG. 13A illustrates ROI 1 to ROI 3 in an initially set area. Inverted triangles C1 to C3 indicate center positions of the ROI 1 to ROI 3. FIG. 13B illustrates an example of moved ROIs after the alignment in step S3456. FIG. 13B illustrates a case where the ROI 1 and the ROI 3 are moved to the right and the ROI 2 is not moved. Thus, the centers C1 and C3 of the ROIs are moved to C1' and C3', respectively. A moving amount of an A-scan may be calculated from moving amounts of ROIs based on moving amounts of the center positions of a neighboring ROI and an ROI. For example, the center position of the ROI 1 is moved from C1 to C1', and the center position of the ROI 2 stays at C2. Here, the X direction moving amount of each A-scan between C1 before the deformation to C2 can be acquired by the following Expression 3.

$$W = 1.0 - \frac{(A\_before - X1)}{(X2 - X1)}$$ [Expression 3]
$$TransX = \Delta X1 * W + \Delta X2 * (1.0 - W)$$
$$A\_after = A\_before - TransX$$

In Expression 3, X1 and X2 are initial center coordinates of ROIs, $\Delta X1$ and $\Delta X2$ are X direction moving amounts of the center coordinates of the ROIs, A_before is a value of an A-scan index before a deformation, and A_after is a value of the A-scan index before the deformation which is referred by A_before. In a case where, for example, A_before is 55 and A_after is 56 as a result of the calculation, the A-scan index 55 contains A-scan data of the A-scan index 56. Expression 3 expresses that a weight for the moving amount varies in accordance with the distances between a plurality of ROIs in an area where the plurality of ROIs overlap. More specifically, in an area where a plurality of ROIs overlap, a weight for a moving amount of the center coordinate of the closest ROI of a plurality of ROIs is higher than a weight for the moving amount of the center coordinate of a farther ROI of the plurality of ROIs.

The moving amount in the Z direction can also be acquired from the moving amounts of the center positions of the ROIs based on the same manner as that of Expression 3, and data move by several pixels in the vertical direction. A_after may have a value that is a real number or an integer. If it is a real number, new A-scan data are generated by a known interpolation method (such as Bilinear or Bicubic) using a plurality of A-scan data pieces. If it is an integer, data of the corresponding A-scan index is referred as it is.

The third alignment unit 335, as described above, corresponds to an example of a determination unit configured to determine a moving amount of a second two-dimensional tomographic image to a first two-dimensional tomographic image in an area having a first area and a second area overlapped based on a positional deviation amount of the first area and a positional deviation amount of the second area.

Step S3458

In step S3458, each A-scan is moved in the X direction and in the Z direction based on the A-scan moving amount acquired in step S3457. Thus, a tomographic image acquired by deforming each A-scan can be generated. It should be noted that not only a tomographic image but also a mask image are deformed with an equal parameter.

Step S3459

In step S3459, whether all tomographic images have undergone a local alignment with respect to a reference image or not is determined. If all images have not been processed, the processing returns to step S3451. If all images have undergone the local alignment, the local alignment processing completes.

This processing is performed by the local alignment. Next, the processing flow returns to FIG. 3B.

Step S346

In step S346, the image composition unit 336 averages a reference tomographic image selected by the image selection unit 334 and a plurality of tomographic images. This averaging process holds, for each pixel, a sum value SUM_A of values acquired by multiplying a plurality of tomographic images by a mask image value and a sum value SUM_B of a plurality of mask image values. Because a mask image stores 0 as an invalid area without having image data because of an alignment, the sum value SUM_B of mask image hold values different from each other between pixels. It is generally assumed that images are moved by several 10 pixels vertically and horizontally because of an alignment. Thus, in a case where N images are used to overlap, the pixel value of SUM_B near the image center is N, and the pixel value of SUM_B of an image end part has a value lower than N.

In this averaging process, SUM_A may be divided by SUM_B to acquire a tomographic image acquired by averaging.

Step S305

In step S305, the detection unit 331 performs a boundary line detection on a high quality tomographic image generated in step S304. The boundary line detection can be performed according to the same method as that in step S341, for example.

Step S306

In step S306, the result of the high quality tomographic image generated by averaging is displayed on the display unit 600.

Step S307

In step S307, an instruction obtaining unit, not illustrated, externally obtains an instruction to complete the imaging of tomographic images by using the image processing system 100 or not. The instruction is input by an operator through the input unit 700. If an instruction to complete the processing is obtained, the image processing system 100 ends the processing. On the other hand, in order to continue the imaging without ending the processing, the process returns to step S302 where the imaging is continued. In this manner, the process is performed by the image processing system 100.

With the aforementioned configuration, according to this embodiment, a local alignment is performed by using boundary lines and image feature values, and, at the same time, a reference image and an addition image are selected for high-quality image generation. Furthermore, for a plurality of two-dimensional tomographic images having undergone an alignment, similarities between corresponding local areas are calculated, and an alignment process is performed area by area. Thus, images for generating a high quality image can be selected. Then, in a case where the retina layer is locally deformed due to, for example, an involuntary eye movements during fixation, alignments are performed division by division of the image. Therefore, a high quality two-dimensional tomographic image can be generated.

Variation Example 1

According to this embodiment, the first alignment unit 332 generates a line projected image and performs an alignment in a horizontal direction (x-axis) on the retina based on an image similarity between line projected images. However, the horizontal direction (x-axis) alignment is not limited thereto. For example, the first alignment unit 332 may detect an edge from a line projected image and may perform an alignment by using a line edge image having the detected edge. Alternatively, the first alignment unit 332 may detect a feature point from a line projected image by using a method such as SIFT (Scale-Invariant Feature Transform) or AKAZE (Accelerated KAZE) and may perform an alignment based on the detected feature point.

Variation Example 2

Figure 14A:
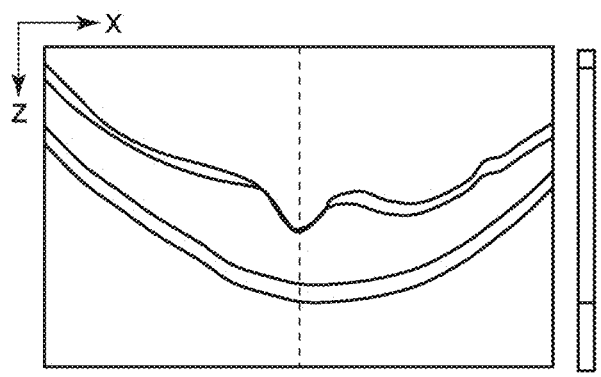
FIGS. 14A to 14D are diagrams for explaining an example of global alignment.
Figure 14B:
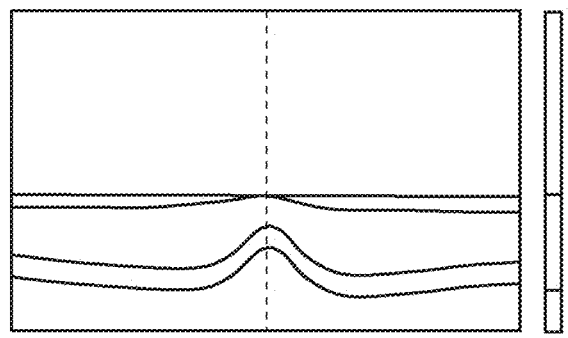
Figure 14C:
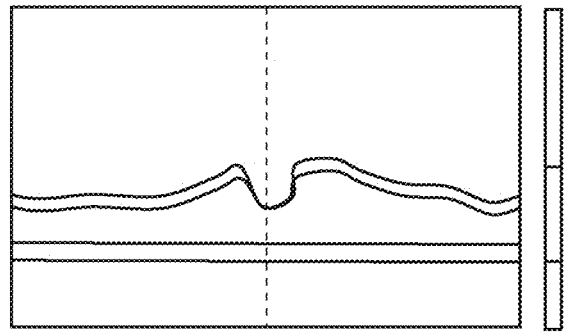

According to this embodiment, the second alignment unit 333 uses boundary line information to perform an alignment in the depth direction (z-axis) on the retina, for example. However, the alignment is not limited to the depth direction (z-axis) alignment. For example, the second alignment unit 333 may generate a horizontal line projected image acquired by averaging a plurality of A-scans in the X-axis direction and may perform an alignment in the depth direction based on the generated projected image. It should be noted that the alignment in this case may use the method according to Embodiment 1 or the method according to Variation Example 1. A horizontal projected image may be generated by using tomographic images as they are imaged. However, a slope may occur in the retina layer in accordance with the state of the imaging. Therefore, the image may be corrected. The correction method in that case may include image deformation such that the shape of the boundary line L1 (ILM) or the boundary line L3 (ISOS) can be flat, for example. FIGS. 14A to 14D illustrate examples of the image correction in that case. FIG. 14A illustrates a tomographic image before a deformation on its left side and illustrates a horizontal line projected image generated from the tomographic image before a deformation on its right side. FIG. 14B illustrates a tomographic image and a horizontal line projected image after a deformation for making L1 to be flat, and FIG. 14C illustrates a tomographic image and a horizontal line projected image after a deformation for making L3 to be flat. For an alignment in the depth direction, a reference location for a boundary line to be deformed during the image deformation operation is not changed, but other locations are deformed. FIGS. 14A to 14D illustrate an example in which the position of the image center (indicated by a broken line) is not changed, but the other parts are deformed. The reference location is not limited to the center of an image. For example, the image center may be defined as an image after the first alignment unit 332 performs a horizontal direction alignment, or an end of the image may be defined as a reference instead. The references are to be aligned between a plurality of images on which a second alignment is to be performed. FIGS. 14A to 14D illustrate an example in which the retina shape is made flat with reference to the boundary line, but embodiments of the present disclosure are not limited thereto. For example, an approximation with a secondary curve may be performed on a detected retina layer, and the retina layer may be deformed to be flat with reference to the approximation curve.

Figure 14D:
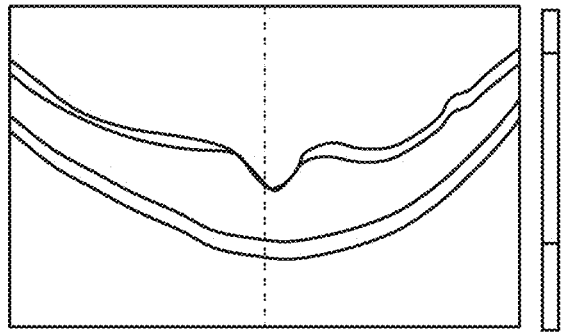

Alternatively, instead of making the retina shape to be flat, a rotating component of the retina layer may only be corrected. FIG. 14D illustrates an example in which a rotation is corrected. FIG. 14D illustrates examples of a tomographic image and a horizontal line projected image deformed such that the positions in the depth direction of the retina layer of both ends of the image can be in alignment with reference to the image center. For the correction, for example, an arbitrary boundary line or an approximation curve may be used to rotate the line about the image, and the tomographic image is rotated such that the positions in the depth direction of the image both ends (X=0, X=the number of A-scans) of the rotated line can be in alignment. Alternatively, correction in the depth direction may be performed on each A-scan based on a difference value between a rotated line and a line before the rotation.

After the slope of the retina layer is corrected by using the method, the horizontal line projected image averaged in the X-axis direction can be generated. By using the horizontal line projected image, the retina layer position in the depth direction can be grasped.

Variation Example 3

According to this embodiment, the third alignment unit 335 performs alignments area by area of the retina in the horizontal direction (x-axis) and the depth direction (z-axis). ROIs for local alignments in this case are set to superimpose on each other, for example. However, ROIs for local alignments may not necessarily superimpose on each other. For example, in a case where an area of a set ROI has a sufficient image feature value, the ROI may be set not to overlap. ROIs to be overlapped and ROIs not to be overlapped may be set in one image simultaneously. An image feature is an example of a result of an analysis on a tomographic image and may include a change of shape, instead of horizontally flat of a blood vessel, a disease, or the retina, for example. A feature of a blood vessel or a disease can be detected from a tomographic image or a line projected image. The retina shape can be grasped by using a boundary line L1 (ILM) or a boundary line L3 (ISOS). It should be noted that because a plurality of tomographic images are images acquired by capturing images of an identical location, a feature may not be detected from all of the plurality of tomographic images but may be detected from a representative one image (such as a reference image).

Alternatively, whether an ROI is to be overlapped or not may be changed simply in accordance imaging angle of view. For example, in imaging with an angle of view as narrow as 3 mm, ROIs may be overlapped because there is a high possibility that the retina shape is imaged to be flat in a wide range of the resulting image. In imaging with an angle of view imaging as wide as 10 mm, ROIs may be overlapped with a small overlapped area or may not be overlapped because there is a high possibility that the retina shape is imaged to be flat only in a part of the resulting image.

Not only changes of an overlapped area of ROIs but also an ROI search range can be dynamically changed in accordance with an image feature or an angle of view.

Variation Example 4

According to this embodiment, the image composition unit 336 generates a mask image for a local alignment in order to remove an invalid area in an averaging process. However, embodiments of the present disclosure are not limited thereto. An invalid area may be detected from a tomographic image without generating a mask image, and the invalid area may be excluded from the averaging calculation.

Variation Example 5

According to this embodiment, an alignment for higher quality OCT images has been described. However, embodiments of the present disclosure are not limited thereto. For example, the present disclosure is applicable to an alignment for OCTA (OCT Angiography). According to OCTA, for visualization of a blood flow part, an identical part is imaged a plurality of number of times, and alignments are performed on the captured images. After that, a change part between the tomographic images is calculated. A change between tomographic images can be calculated by calculating a decorrelation, for example. By calculating such a decorrelation, a moving part (such as a blood flow) only remains and may be visualized to generate an OCTA image. The present disclosure is also applicable to a tomographic image alignment for the OCTA image generation.

Variation Example 6

Having described, according to this embodiment, operations from imaging to display are described as a flow, embodiments of the present disclosure are not limited thereto. For example, data that have already been imaged may be used to perform the high-quality image generation process. In this case, the processing relating to the imaging may be skipped, but, instead, a plurality of tomographic images that has been already imaged may be obtained. Then, the high-quality image generation process is performed in step S304.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-172333 filed Sep. 7, 2017, which is hereby incorporated by reference herein in its entirety.

What is claimed is:

1. An image processing apparatus comprising:
    a first alignment unit configured to perform an alignment in a direction intersecting with a depth direction of an eye on a plurality of two-dimensional tomographic images using information regarding to a positional deviation amount obtained by comparing projected images in the depth direction obtained using information regarding to the plurality of the two-dimensional tomographic images, the plurality of two-dimensional tomographic images being obtained based on measurement light controlled to scan an identical position of the eye; and
    a second alignment unit configured to perform an alignment in the depth direction on the plurality of two-dimensional tomographic images.

2. The image processing apparatus according to claim 1, wherein the second alignment unit performs the alignment in the depth direction on the plurality of two-dimensional tomographic images using information regarding to a positional deviation amount obtained by comparing layer boundaries obtained using information regarding to the plurality of two-dimensional tomographic images.

3. The image processing apparatus according to claim 2, wherein the second alignment unit performs the alignment in the depth direction on the plurality of two-dimensional tomographic images based on a positional deviation amount of layer boundaries obtained from a plurality of regions dividing the two-dimensional tomographic image in the direction intersecting with the depth direction.

4. The image processing apparatus according to claim 3, wherein the second alignment unit selects a predetermined number of positional deviation amounts from positional deviation amounts of the layer boundaries in the plurality of regions such that a value indicating a variation of the positional deviation amount in a predetermined number of combinations is at a minimum, and performs the alignment in the depth direction on the plurality of two-dimensional tomographic images based on a representative value of the selected positional deviation amounts.

5. The image processing apparatus according to claim 4, wherein the value indicating a variation includes a variance or a standard deviation; and
wherein the value includes an average value or a median value.

6. The image processing apparatus according to claim 1, further comprising:
an image selection unit configured to select a reference image being a reference for an alignment from the plurality of two-dimensional tomographic images,
wherein the image selection unit selects the reference image based on at least one of (a) a result of a comparison between projected images in the depth direction obtained from the plurality of two-dimensional tomographic images and (b) a result of a comparison between layer boundaries obtained from the plurality of two-dimensional tomographic images.

7. The image processing apparatus according to claim 6, wherein the result of the comparison between projected images in the depth direction obtained from the plurality of two-dimensional tomographic images includes a similarity between the projected images; and
wherein the result of the comparison between layer boundaries obtained from the plurality of two-dimensional tomographic images includes a positional deviation amount of the layer boundaries.

8. The image processing apparatus according to claim 7, wherein the image selection unit selects the reference image based on, in a case where one two-dimensional tomographic image and a plurality of other two-dimensional tomographic images are compared in the plurality of two-dimensional tomographic images, one of a number of two-dimensional tomographic images having a predetermined threshold or higher value of similarity and having a predetermined threshold or lower positional deviation amounts of the layer boundaries and a number of two-dimensional tomographic images having a predetermined or higher number of regions dividing each of the two-dimensional tomographic images in the direction intersecting with the depth direction, the regions having a predetermined threshold or lower positional deviation amounts of the layer boundaries.

9. The image processing apparatus according to claim 6, further comprising:
a third alignment unit configured to perform an alignment on the plurality of two-dimensional tomographic images having undergone the alignment by the first alignment unit and the second alignment unit with reference to the reference image; and
an image selection unit configured to select a reference image for the alignment to be performed by the third alignment unit from the plurality of two-dimensional tomographic images.

10. The image processing apparatus according to claim 9, further comprising a generation unit configured to generate an averaged image by averaging the plurality of two-dimensional tomographic images having undergone an alignment by the third alignment unit.

11. The image processing apparatus according to claim 9, wherein an OCTA (Optical Coherence Tomography Angiography) image is generated from the plurality of two-dimensional tomographic images having undergone an alignment by the third alignment unit.

12. An alignment method comprising:
performing an alignment in a direction intersecting with a depth direction of an eye on a plurality of two-dimensional tomographic images using information regarding to a positional deviation amount obtained by comparing projecting images in the depth direction obtained using information regarding to the plurality of two-dimensional tomographic images, the plurality of two-dimensional tomographic images being obtained based on measurement light controlled to scan an identical position of the eye; and
performing an alignment in the depth direction on the plurality of two-dimensional tomographic images.

13. A non-transitory computer-readable storage medium storing a program for causing a computer to execute the method according to claim 12.

14. An image processing apparatus comprising:
a first alignment unit configured to perform an alignment in a direction intersecting with a depth direction of an eye on a plurality of two-dimensional tomographic images, the plurality of two-dimensional tomographic images being obtained based on measurement light controlled to scan an identical position of the eye;
a second alignment unit configured to perform an alignment in the depth direction on the plurality of two-dimensional tomographic images; and
an image selection unit configured to select a reference image being a reference for an alignment from the plurality of two-dimensional tomographic images using at least one of (a) a result of a comparison between projected images in the depth direction obtained using information regarding to the plurality of two-dimensional tomographic images and (b) a result of a comparison between layer boundaries obtained information regarding to the plurality of two-dimensional tomographic images.

15. The image processing apparatus according to claim 14, wherein the first alignment unit performs the alignment in the direction intersecting with the depth direction on the plurality of two-dimensional tomographic images using information regarding to a positional deviation amount obtained by comparing projected images in the depth direction obtained using information regarding to the plurality of two-dimensional tomographic images.

16. An alignment method comprising:
performing an alignment in a direction intersecting with a depth direction of an eye on a plurality of two-dimensional tomographic images, the plurality of two-dimensional tomographic images being obtained based on measurement light controlled to scan an identical position of the eye;
performing an alignment in the depth direction on the plurality of two-dimensional tomographic images; and
selecting a reference image being a reference for an alignment from the plurality of two-dimensional tomographic images using at least one of (a) a result of a comparison between projected images in the depth direction obtained using information regarding to the plurality of two-dimensional tomographic images and (b) a result of a comparison between layer boundaries obtained information regarding to the plurality of two-dimensional tomographic images.

17. A non-transitory computer-readable storage medium storing a program for causing a computer to execute the method according to claim 16.

18. An image processing apparatus comprising:
a first alignment unit configured to perform an alignment in a direction intersecting with a depth direction of an eye on a plurality of two-dimensional tomographic images, the plurality of two-dimensional tomographic images being obtained based on measurement light controlled to scan an identical position of the eye; and
a second alignment unit configured to perform an alignment in the depth direction on the plurality of two-dimensional tomographic images using information regarding to a positional deviation amount obtained by comparing layer boundaries obtained using information regarding to the plurality of two-dimensional tomographic images.

19. An alignment method comprising:
performing an alignment in a direction intersecting with a depth direction of an eye on a plurality of two-dimensional tomographic images, the plurality of two-dimensional tomographic images being obtained based on measurement light controlled to scan an identical position of the eye; and
performing an alignment in the depth direction on the plurality of two-dimensional tomographic images using information regarding to a positional deviation amount obtained by comparing layer boundaries obtained using information regarding to the plurality of two-dimensional tomographic images.

20. A non-transitory computer-readable storage medium storing a program for causing a computer to execute the method according to claim 19.

* * * * *